United States Patent [19]

Weeks

[11] Plant 4,700

[45] Apr. 28, 1981

[54] HYBRID TEA ROSE HAVING FLOWERS OF BRILLIANT SIGNAL RED TO SCARLET RED COLORING AND VISIBLE VEINING

[76] Inventor: O. L. Weeks, 4759 Philadelphia St., Chino, Calif. 91710

[21] Appl. No.: 140,196

[22] Filed: Apr. 14, 1980

[51] Int. Cl.[3] ..... A01H 5/00

[52] U.S. Cl. ..... Plt./20

[58] Field of Search ..... Plt./20

*Primary Examiner*—Robert E. Bagwill

*Attorney, Agent, or Firm*—Vincent G. Gioia

[57] ABSTRACT

A new hybrid tea rose having flowers of brilliant signal red to scarlet red coloring and visible veining.

1 Drawing Figure

1

The present invention relates to a new and distinct variety of rose plant of the hybrid tea rose class, which was originated by my crossing as seed and pollen parents, unnamed, unpatented and unreleased seedlings of my creation.

Among the novel characteristics possessed by this new variety which distinguish it from its parents and all other varieties of which I am aware are many petaled blooms of bright red, non-fading, coloring borne on very long stems and a vigorous, free branching plant with abundant foliage and good disease resistance. Flowers are exceptionally long lasting on the plant and as a cut flower. Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusually fine hybrid tea rose with blooms of good form displayed on a vigorous, upright, free branching plant with abundant foliage. The flowers are of heavy petalage but open well. The brilliant red coloring holds well upon aging; although outer petals may lighten slightly.

The seed and pollen parents both differ from the new variety in growth habit with both not being as vigorous or producing as good or as large a plant. The new rose is more vigorous and grows taller than both parents. The bright signal red and scarlet red flower coloring of the new rose is also different.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "46A" is plate 46A of the Royal Horticultural Society Color Chart.

Parentage: Seedling.

*Seed parent.*—Unnamed, unreleased seedling.

*Pollen parent.*—Unnamed, unreleased seedling.

Class: Hybrid tea.

2

The following observations are made of specimens grown outdoors in San Bernardino County, Calif. during the month of October.

I. FLOWER

Blooming habit: Intermittent to continuous.

A. Bud:

(1) *Size.*—Medium.

(2) *Form.*—Pointed, oval.

(3) *Color.*—As calyx breaks and when sepals first divide—46A. When petals begin to unfurl—46A.

(4) *Sepals.*—Simple, with foliacious appendages extending beyond tip of bud.

(5) *Peduncle.*—Length—medium. Aspect—conspicuous. Strength—erect. Color—reddish green at first becoming green 138B.

B. Bloom:

(1) *Size.*—Average size when fully expanded—about 4½-inches to 5-inches.

(2) *Borne.*—Singly and in clusters of 2 to 4 blooms.

(3) *Form.*—Urn shaped to cupped becoming flat upon opening.

(4) *Petalage.*—Number of petals under normal conditions—about 46 to 50.

(5) *Color.*—Bud color begins as currant red 46A. As petals unfurl to ⅓-½ open bloom, color lightens to signal red 43A and scarlet 43B. Higher density coloring affect appears at center of partially-opened blooms due to concentration of petals. As blooms open further, outer petals appear to lighten to 42B and 42C. Individual petals display marked veining, becoming more evident in color contrast as petals age and lighten. Occasional white streaking is seen on outer petals.

C. Petals:

(1) *Texture.*—Thick.

(2) *Appearance.*—Leathery, top surface satiny.

(3) *Form.*—Slightly rounded.

(4) Arrangement.—Slightly irregular.

(5) *Petaloids in center.*—Few.

(6) *Persistence.*—Drop off cleanly.

(7) *Fragrance.*—Slight.

(8) Lasting quality.—3 to 5 days on plant and as cut flower.

2. REPRODUCTIVE ORGANS

A. Stamens, filaments and anthers:

(1) *Arrangement.*—Stamens irregularly about pistils.

(2) *Color.*—Short filaments, yellow base, reddish most with yellow anthers.

B. Pollen: Color—yellow.

C. Styles: Even, medium, bunched.

D. Stigmas: Color—light yellow.

E. Hips: None observed.

3. PLANT

A. Form: Upright, tall.

B. Growth: Vigorous, free branching.

C. Foliage: Compound 3 to 7 leaflets.

(1) *Size.*—Medium.

(2) *Quantity.*—Abundant.

(3) *Color.*—New foliage: Reddish colored 59A with green tones becoming green upon maturing (136C). Old foliage: Upper side—near to 136A. Under side—near to 191A.

(4) *Shape.*—Ovoid, base round.

(5) *Texture.*—Leathery.

(6) *Edge.*—Serrated.

(7) *Serration.*—Simple.

(8) *Leaf stem.*—Color—near to 138A. Under side—138B.

(9) *Stipules.*—Long.

(10) *Resistance to disease.*—Mildew—good. Rust—good.

D. Wood (1) *New wood.*—Color—near 138A. Bark—smooth, shiny.

(2) Old wood.—Color—near 137A. Bark—smooth, shiny.

E. Thorns:

(1) *Thorns.*—Quantity (main stalk): Ordinary. On laterals from stalk—few. Form—straight. Length—medium. Color—138B. Position—scattered.

(2) Prickles.—Few.

F. Winter hardiness: Good winter hardiness.

I claim:

1. A new and distinct variety of rose plant of the hybrid tea class, substantially as shown and described, characterized particularly by bright signal red to scarlet red flowers with visible veining which are long lasting on the plant and as cut flowers.

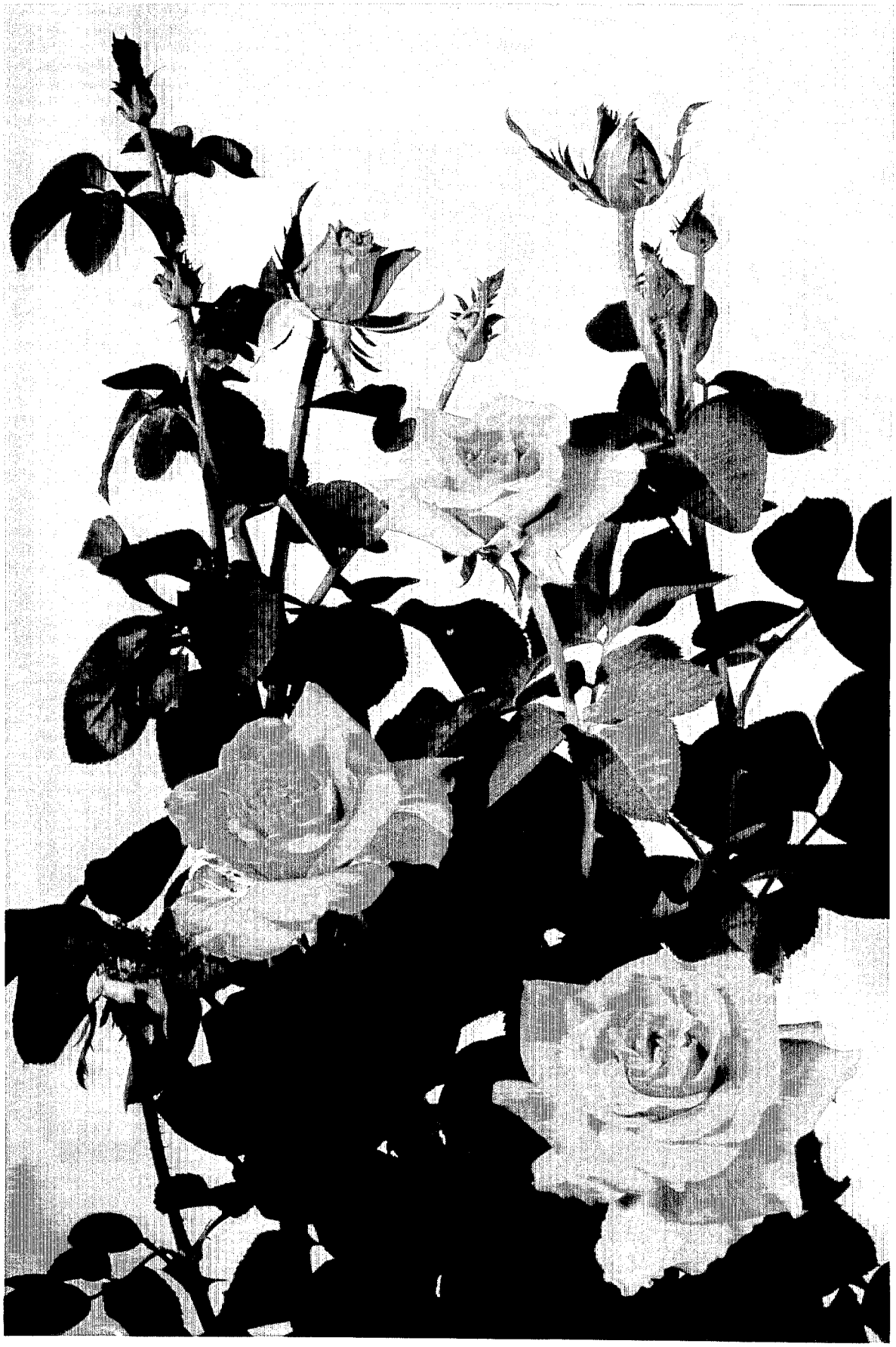

* * * * *